United States Patent [19]
Shu

[11] Patent Number: 5,591,134
[45] Date of Patent: Jan. 7, 1997

[54] PROTECTIVE NEEDLE COVER

[76] Inventor: Han C. Shu, 5F, 205 Wu Shin Street, Taipei, Taiwan

[21] Appl. No.: 496,223

[22] Filed: Jun. 28, 1995

[51] Int. Cl.$^6$ ........................................................ A61M 5/32
[52] U.S. Cl. ............................................. 604/192; 604/263
[58] Field of Search ................................. 604/192, 187, 604/263, 110

[56] References Cited

U.S. PATENT DOCUMENTS

| | | | |
|---|---|---|---|
| 4,888,001 | 12/1989 | Schoenberg | 604/192 X |
| 4,909,792 | 3/1990 | Norelli | 604/263 X |
| 4,966,591 | 10/1990 | Yuen | 604/192 |
| 5,188,612 | 2/1993 | Herrington, Jr. et al. | 604/192 |

*Primary Examiner*—John D. Yasko
*Attorney, Agent, or Firm*—Beveridge, DeGrandi, Weilacher & Young LLP

[57] ABSTRACT

Disclosed is a protective needle cover having a cylindrical body which consists of two pivotally connected halves such that one of the halves is turnable relative to the other half and opens the cylindrical body for a needle to be conveniently and angularly positioned in the protective needle cover. The openable two halves are provided on their free edges at corresponding positions with a set of fastening means such that the cylindrical body of the protective needle cover can be opened or closed simply by using two fingers. When the halves of the cylindrical body are opened by disengaging the fastening means, a needle can be safely put between the opened halves at a certain angle. Then, the halves can be closed again and fastened to each other to form the complete cylindrical body of the protective needle cover. A used needle can therefore, be held in the cover without unexpectedly and dangerously hurting an operator.

4 Claims, 8 Drawing Sheets

PROTECTIVE NEEDLE COVER

BACKGROUND OF THE INVENTION

The present invention relates to a protective needle cover, and more particularly to a protective needle cover having two pivotally connected side walls which can be turned relative to each other so that the protective needle cover is widely opened to accommodate a needle therein and the chances of the needle to dangerously stab an operator is reduced.

Injection by means of a syringe with a needle is one of a very important and necessary means in medical treatment. The needle for injection usually has a pointed end which shall very possibly threaten an operator or any other people involving in the use or disposal of such needle if it is not carefully and effectively handled in a safe manner. A minor danger possibly caused by a used needle is, for example, stabbing and hurting the operator. And, a serious danger includes, for example, giving the stabbed person an infectious disease by agency of the contaminated needle. In an age being threatened by AIDS, it is a very important thing and requires special care of any medical personnel to dispose the used and contaminated needle with an effective and safe way.

A conventional and widely adopted way of safely handling a needle is to cover the needle with a hard, cylindrical case. To use the needle, first remove the hard case from the needle from a top thereof. After the use of the needle is completed, the hare case is replace over the needle before the needle is discarded. Due to the thin and elongated body of the needle, the operator is frequently unexpectedly stabbed by the needle when the hard case is quickly replaced over the needle.

Figure 1:
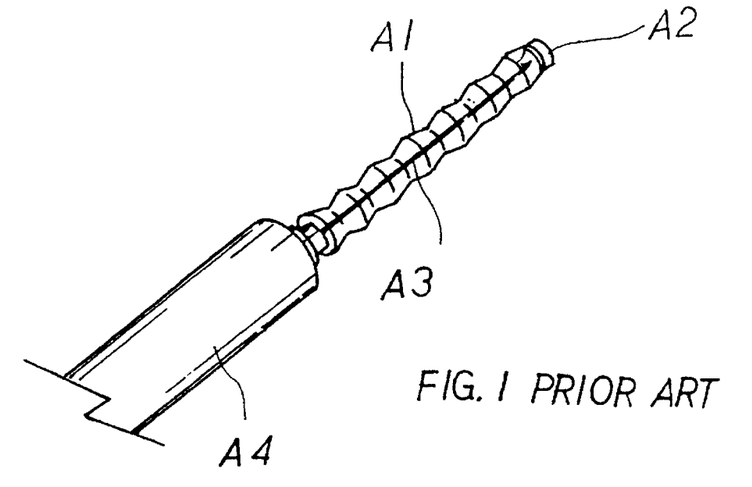
FIG. 1 illustrates a conventional flexible safety needle cover.

FIG. 1 illustrates a conventional safety needle cover A1 which mainly consists of a long tubular member formed of multiple continuous flexible segments and a rubber stopper A2 disposed at a front end of the tubular member A1. The flexible tubular member A1 is put around a needle A3 to prevent the latter from being exposed to the atmosphere and stabbing any person. In this safety needle cover, the rubber stopper A2 does not have any preformed hole on it when it is formed to be covered around a needle. However, when the needle covered by the tubular member A1 is to be used, the rubber stopper A2 is pierced through by the pointed tip of the needle A3 so that the needle A3 is exposed to the outside. In a similar manner, an outcoming force applied on the flexible tubular member A1 may also carelessly cause the needle A3 to pierce through the rubber stopper A2 and thereby causes any dangerous result. Moreover, it is necessary to use two hands when operating this safety needle cover A1, that is, one hand is used to hold a syringe A4 to which the needle A3 is connected while the other hand is used to squeeze the small rubber stopper A2 in front of the pointed end of the needle A3. This is of course dangerous to handle the needle and the safety needle cover in such a manner.

Figure 2:
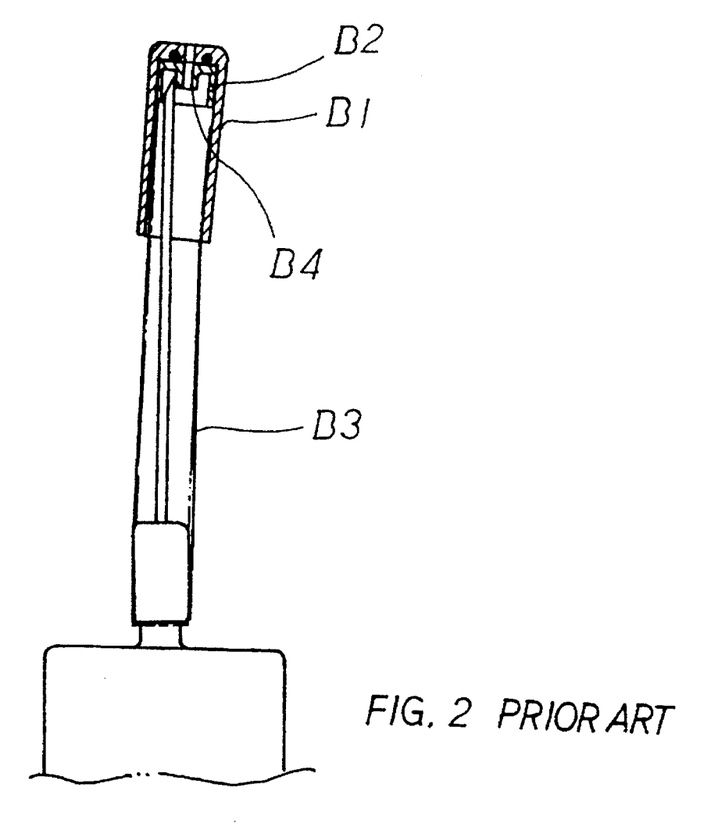
FIG. 2 illustrates another conventional extensible safety needle cover.

FIG. 2 illustrates another conventional safety needle cover comprising an outer sleeve B1, an inner sleeve B2, and an elastic cover B3. The outer sleeve B1 is cylinder-shaped and in a proper length. A hole is formed on a top surface of the outer sleeve B1 for a needle to pass therethrough.

The inner sleeve B2 has an opening formed on a top surface thereof. A circle of downward extended flange portion B4 is provided around a bottom side of the opening of the inner sleeve B2, such that a space is formed between the flange portion B4 and the peripheral side wall of the inner sleeve B2. The elastic cover B3 has proper tensility and is collapsed to a root portion of the needle before the needle is put to use. When the needle has been used, the sleeves B1 and B2 are pulled upward along the needle so that the tip of the needle is restricted to the space defined by the flange portion B4 and the side wall of the inner sleeve B2, as shown in FIG. 2.

In the conventional safety needle cover illustrated in FIG. 2, an existed disadvantage is that the outer sleeve B1 must be pushed forward with fingers and therefore, the fingers are easily subject to dangerous stabbing. Since the outer sleeve B1 has very small area, fingers squeezing it to extend it are easily carelessly stabbed and injured by the needle to be covered by the sleeves. Moreover, it is hard to assemble such a conventional needle cover and a higher manufacturing cost is required for forming it.

SUMMARY OF THE INVENTION

It is therefore a primary object of the present invention to provide a protective needle cover, an operation of which would not cause an operator to be stabbed by the needle. The protective needle cover according to the present invention is mainly characterized by a cylindrical body consisting of two axially, pivotally connected side walls. The two side walls may be turned relative to each other so as to widely open the cylindrical body and allow a needle to be angularly and conveniently put into the cylindrical body of the protective needle cover. At least one set of fastening means is provided on the free edges of the two side walls. By compressing the two side walls at positions near the fastening means with two fingers, the opened side walls can be easily but firmly closed together to enclose the needle therein without unexpectedly and dangerously stabbing an operator.

Another object of the present invention is to provide a protective needle cover having two openable side walls, wherein recess portions suitable for holding by fingers are provided on each of the side walls near the free edges thereof.

A further object of the present invention is to provide a protective needle cover having fastening means provided at free edges of two openable side walls, wherein the fastening means can be put to a closed state by compressing the two side walls toward each other and to an open state again by further compressing the two side walls.

The protective needle cover according to the present invention can also be used without first disengaging the closed fastening means. That is, the present invention can be put over and around a needle in the same way as that adopted to cover a conventional safety needle cover around a needle.

BRIEF DESCRIPTION OF THE DRAWINGS

FIGS. 6A and 6B are fragmentary, enlarged, sectional views showing the fastening means of the present invention, wherein FIG. 6A shows the fastening means in an engaged state, and FIG. 6B shows the fastening means in a disengaged state;

DETAILED DESCRIPTION OF THE PREFERRED EMBODIMENTS

Figure 3:
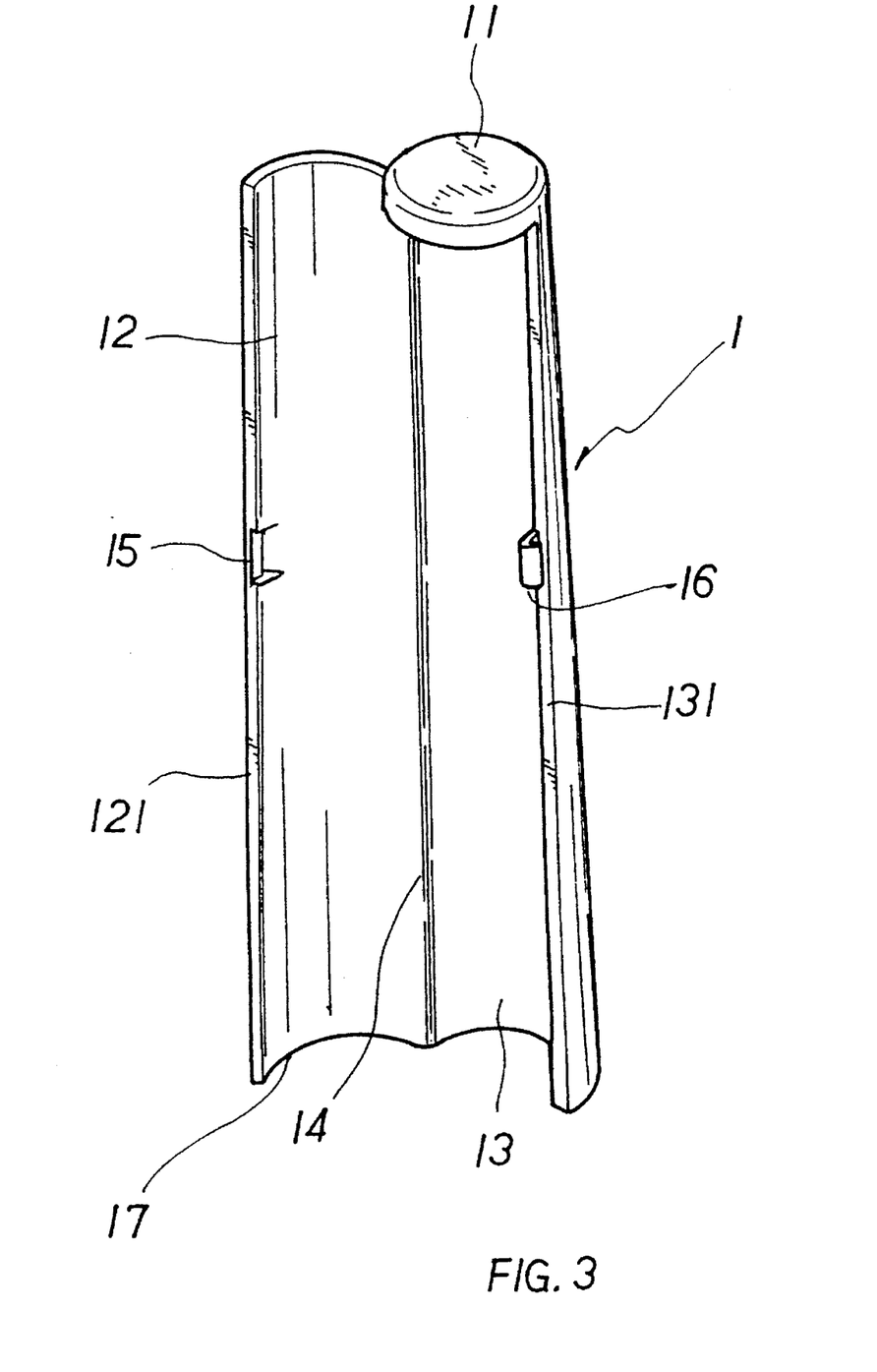
FIG. 3 illustrates a protective needle cover according to a first embodiment of the present invention, wherein the protective cover is in an open state.
Figure 4:
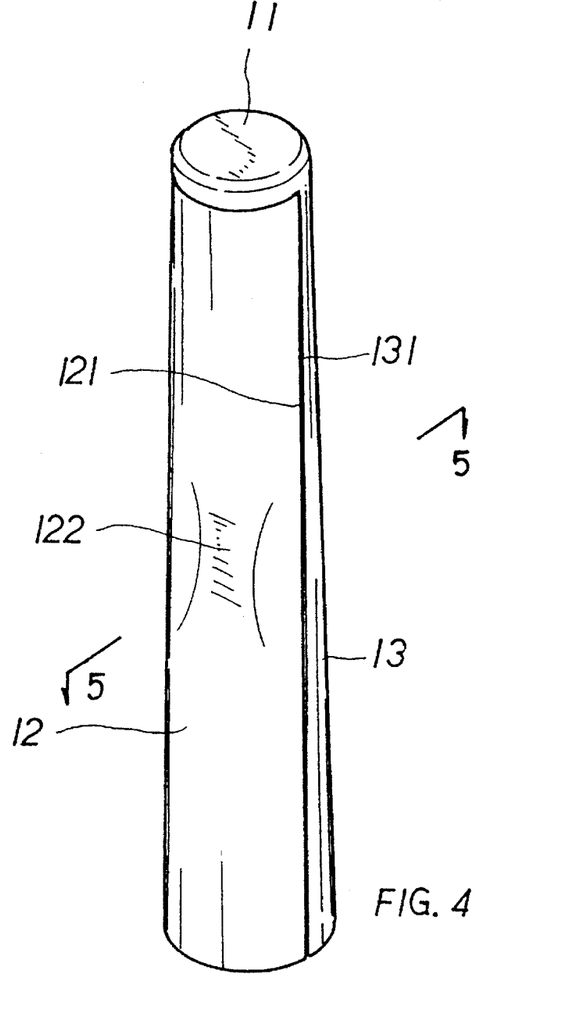
FIG. 4 illustrates the protective needle cover of FIG. 3 but in a closed state forming a complete cylindrical body.

Please refer to FIG. 3 in which a first embodiment of the present invention is shown. The present invention is a protective needle cover substantially in the form of a long cylindrical body 1. The cylindrical body 1 has a top portion 11 which is a full circle, and an axially extended side wall portion which is divided into two halves 12, 13. The two halves 12, 13 of the side wall portion of the cylindrical body 1 are axially and pivotally connected together at one side by means of a connection portion 14 such that any one of the two halves 12, 13 is turnable about the connection portion 14 to be opened relative to the other half. The entire protective needle cover can be made of plastic material by injection molding. A retaining hole 15 and a projected hook 16 are separately but correspondingly provided on the two halves 12, 13 at their detachably connected free edges 121, 131, respectively, forming a set of fastening means to engage and/or disengage the two halves 12, 13. The retaining hole 15 and the projected hook 16 are so formed that they can firmly engage with each other when forces are externally applied to the two halves 12, 13 in opposite directions to press them against each other. The closed and engaged two halves 12, 13 together with the round top portion 11 form the protective needle cover in the form of a long cylindrical body 1 as shown in FIG. 4.

Figure 5:
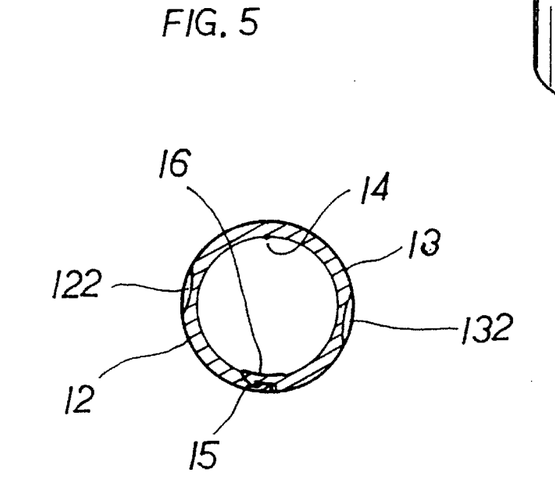
FIG. 5 is a cross sectional view taken on line 5—5 of FIG. 4.

FIG. 5 illustrates a cross section of the closed cylindrical body 1, specially showing the engagement of the retaining hole 15 with the projected hook 16. To enhance the engagement of the two halves 12, 13, additional set or sets of fastening means consisting of the retaining hole 15 and the projected hook 16 can be provided.

Moreover, recess portions 122, 132 can be selectively provided on the two halves 12, 13, respectively, at adequate positions for a user to more conveniently hold the cylindrical body 1 with fingers.

Figure 6A:
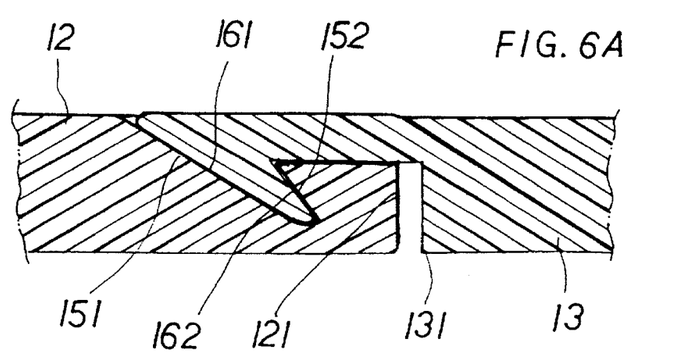
Figure 6B:
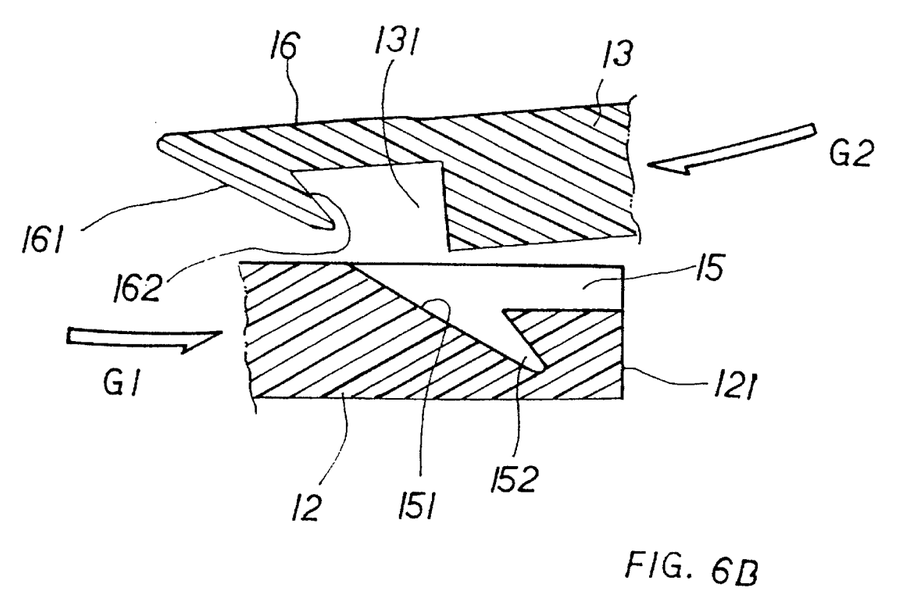

FIGS. 6A and 6B are fragmentary, enlarged, sectional views showing the manner in which the projected hook 16 engages with the retaining hole 15. The retaining hole 15 has a profile forming a counterpart of the projected hook 16. The detachably connected free edges 121, 131 of the two halves 12, 13, respectively, may check with and stop each other to connect the two halves 12, 13 together. The retaining hole 15 is formed with a sliding surface 151 and an end retaining portion 152. The projected hook 16 is formed with an inclined front surface 161 and an inclined inner surface 162 opposite to the inclined front surface 161. When in an engaged position, the sliding surface 151 of the retaining hole 15 fitly contacts with the inclined front surface 161 of the projected hook 16, and the inclined inner surface 162 extends into and fitly contacts with the end retaining portion 152. A purpose of providing the inclined front surface 161 and the inclined sliding surface 151 is to allow the engaged projected hook 16 and the retaining hole 15 to successfully disengage from each other when the two engaged halves 12, 13 of the protective needle cover are further subjected to forces in the directions as shown by the arrows G1, G2, respectively, in FIG. 6B. More particularly, when two opposed forces separately indicated by arrows G1, G2 are respectively applied on the engaged halves 12, 13, the half 13 is pushed to move in the direction of arrow G2 and thereby the inclined front surface 161 of the projected hook 16 slides along the inclined sliding surface 151 of the retaining hole 15 until the inclined inner surface 162 of the projected hook 16 completely moves out of the end retaining portion 152 of the retaining hole 15.

Since the entire protective needle cover of the present invention can be made of plastic material by injection molding without the need of any other parts or components, the protective needle cover can be manufactured at considerably low cost which is, of course, a competitive advantage of the present invention.

Figure 7:
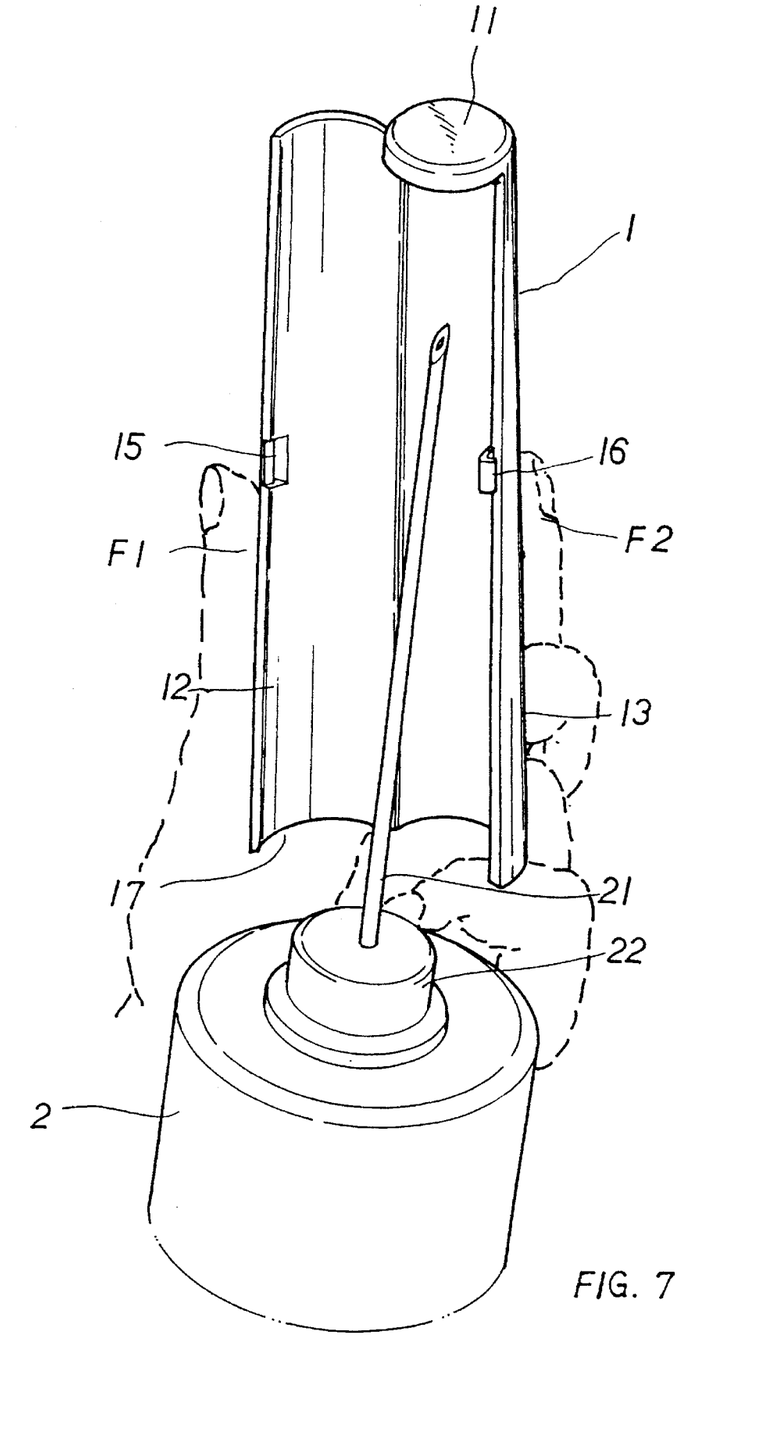
FIG. 7 shows a needle being slightly angularily put into an opened protective needle cover of FIG. 3.

To use the protective needle cover of the present invention, it is a basic and first movement to close the two halves 12, 13 together and thereby forms the cylindrical body 1 as shown in FIG. 4 to accommodate a needle therein. To use a syringe 2 whose needle 21 is covered by a protective needle cover according to the present invention, just remove the closed cover from the syringe 2 to expose the needle 21. When the use of the needle 21 is completed and the needle 21 is to be disposed by receiving it into the protective needle cover again, first compress the cylindrical body 1 from two lateral sides thereof to cause the two halves 12, 13 thereof to disengage from each other, and thereby, separates the two halves 12, 13 from their detachably connected free edges 121, 131, respectively. Then, put the used needle 21 into the opened cylindrical body 1 between the two halves 12, 13 with the needle 21 in a slightly inclined position, as shown in FIG. 7. Finally, use two fingers F1, F2 to compress the two halves 12, 13 at where the retaining hole 15 and the projected hook 16 are located, causing the projected hook 16 to slide into and fitly engage with the retaining hole 15, so that the used needle 21 is enclosed in the closed cylindrical body 1.

The protective needle cover of the present invention has a bottom rim 17 having an inner diameter corresponding to an outer diameter of a projected seat 22 in front of the syringe 2. The needle 21 is centered on the projected seat 22. When the protective needle cover is closed through the set of fastening means and is put around the projected seat 22, the engaged fastening means is not subject to easy disengagement because the two halves 12, 13 of the cylindrical body 1 are prevented from further moving toward each other by any outcoming forces due to the contact of the bottom rim 17 of the cylindrical body 1 with the projected seat 22 in front of the syringe 2.

Figure 8:
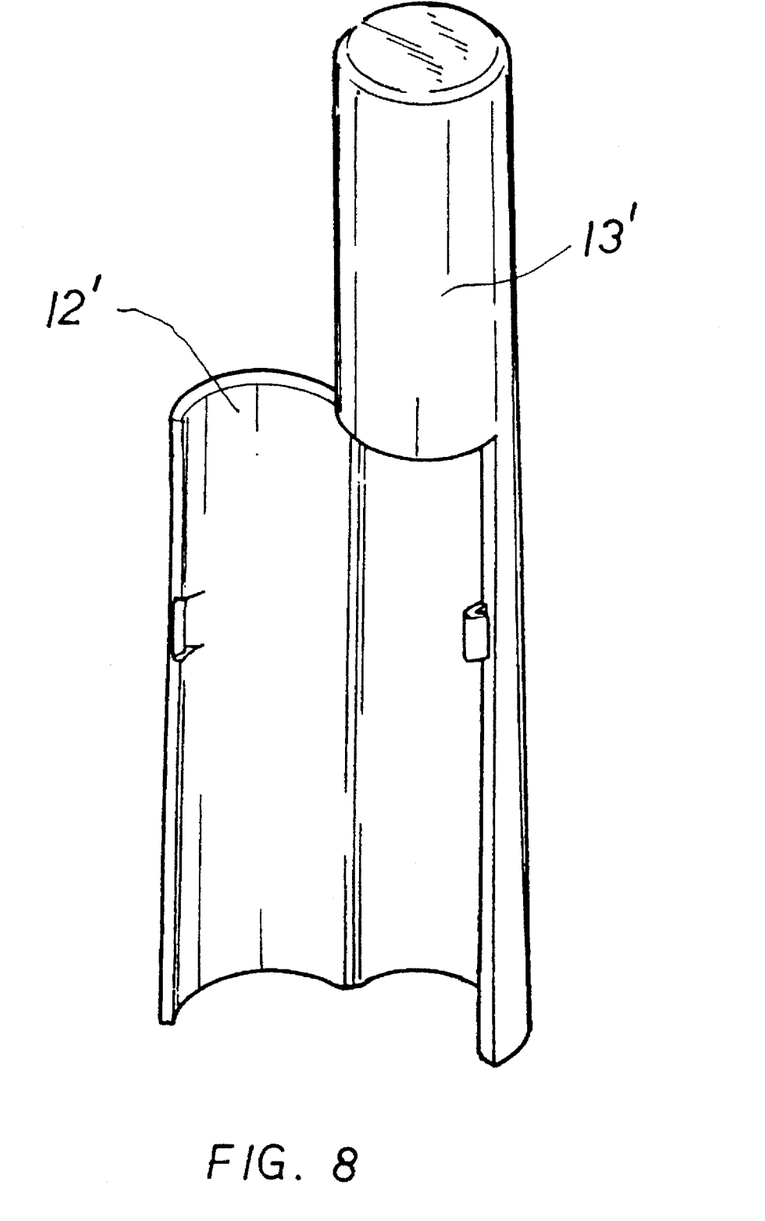
FIG. 8 illustrates a protective needle cover according to a second embodiment of the present invention.

FIG. 8 illustrates a second embodiment of the present invention in which the cylindrical body 1 has a pivotally openable part 12' having a length less than a full length of the cylindrical body 1. The part 12' extends from the bottom rim of the cylindrical body 1 to a certain height of the cylindrical body 1, so that the protective needle cover has a top portion 13' which always keeps in a cylindrical shape. A used needle 21 can therefore be completedly extended into the cylindrical top portion 13' without the risk of unexpectedly and dangerously stabbing any operator.

Figure 9:
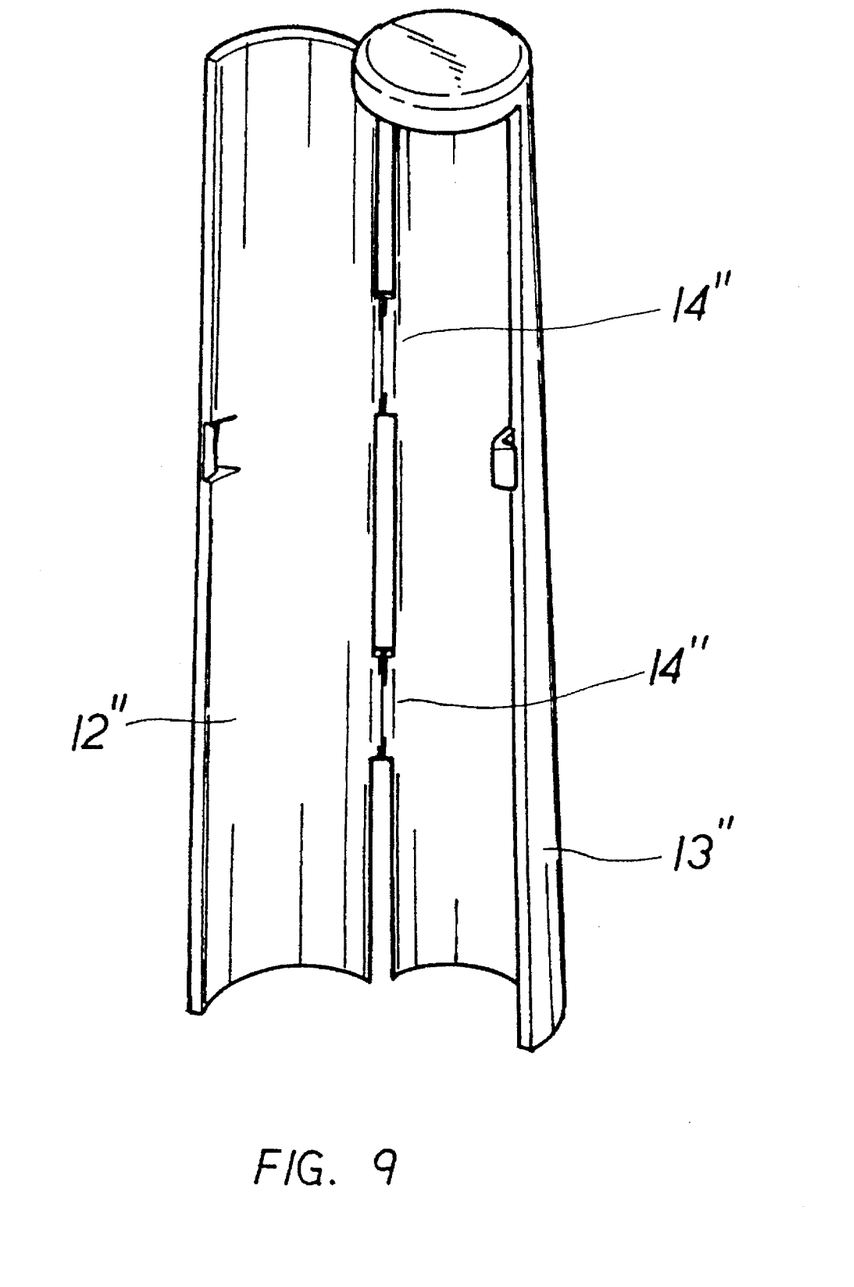
FIG. 9 illustrates a protective needle cover according to a third embodiment of the present invention.

FIG. 9 illustrates a third embodiment of the present invention in which the cylindrical body 1 has two halves 12", 13" connected by means of strip-shaped connection portions 14". The connection portions 14" project from the cylindrical body 1 when the two halves 12", 13" are closed by the fastening means provided on the two halves. The projected connection portions 14" permit the cylindrical protective needle cover to be stably positioned on a plane with the two detachably connected free edges 121, 131 of the two halves 12", 13", respectively, automatically facing upward away from the plane on which the protective needle cover is positioned while the projected connection portions 14" contact with the plane. Thereby, the protective needle cover can be conveniently picked up with just two fingers of the operator for use.

Figure 10:
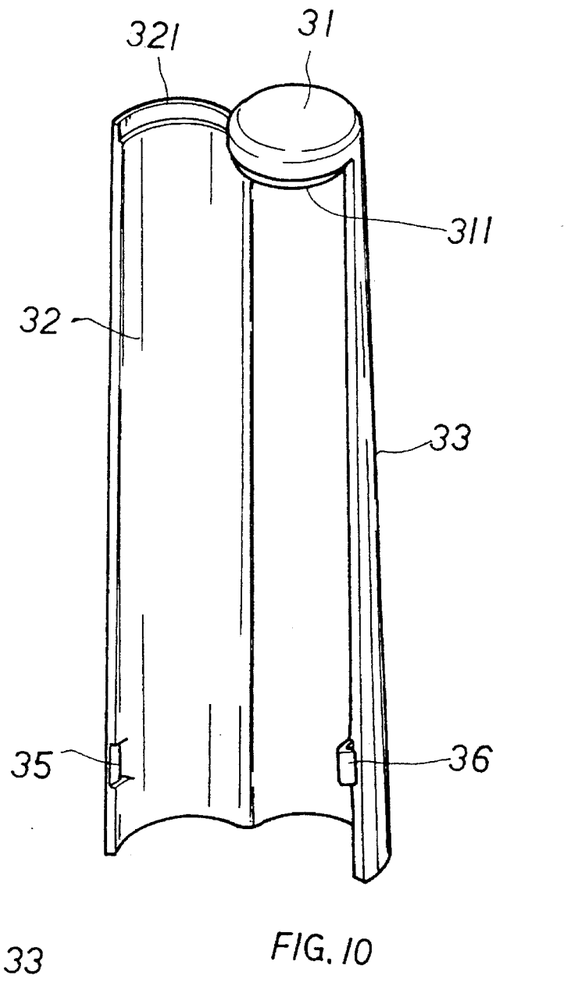
FIG. 10 illustrates a protective needle cover according to a fourth embodiment of the present invention.
Figure 11:
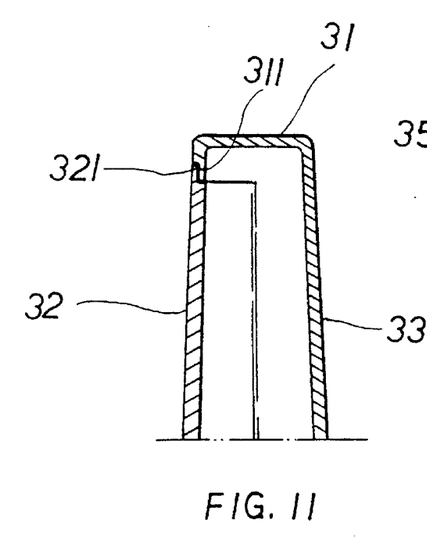
FIG. 11 is a sectional view showing the protective needle cover of FIG. 10 in a closed cylindrical state.

FIG. 10 illustrates a fourth embodiment of the present invention in which the protective needle cover has two pivotally connected halves 32, 33. The half 33 has a top portion 31 forming a closed end of the cover. The top portion 31 has a diameter-reduced lower portion 311 corresponding to a diameter-increased upper portion 321 of the other half 32 and thereby allows the half 32 to fitly close to the half 33 when the two halves are closed to each other to form a cylindrical body of the protective needle cover as shown in FIG. 11. The fitly contact and engagement of the portion 321 with the portion 311 provides a secondary stop means to permit the two halves 32, 33 to maintain in a closed state even when the two halves are subjected to a rather big force at this particular area. The two halves 32, 33 are respectively provided with a retaining hole 35 and a projected hook 36 at a lower position compared to that of the other embodiments of the present invention. This lower position of the retaining hole 35 and the projected hook 36 shall allow the retaining hole 35 and the projected hook 36 to easily disengage from each other in the way as shown in FIG. 6B without being adversely hindered by the engagement of the portion 311 with the portion 321.

What is claimed is:

1. A protective needle cover for covering a front end of a syringe over a pointed needle thereof, consisting essentially of a substantially cylindrical body which has a bottom rim having an inner diameter corresponding to an outer diameter of a projected seat in front of said syringe for fixing said needle thereto, and a fully circular top surface sealing a top end of said cylindrical body, said cylindrical body having a first half side wall and a second half side wall both axially extending a full length of said cylindrical body and being pivotally connected together at a first edge thereof by means of a connection portion axially extending between them, said first half side wall being formed at a second edge opposite to said first edge with at least a projected portion at a position corresponding to said retaining hole, said second half side wall being formed at a second edge opposite to said first edge with at least a projected portion at a position corresponding to said retaining hole on said first half side wall, whereby said retaining hole and said projected portion are engaged with each other when two opposed forces are applied on them and thereby join said second edges of said first half side wall with said second half side wall to close said cylindrical body, and said retaining hole and said projected portion are disengaged from each other to permit said first half side wall to pivotally turn about said connection portion to separate from said second half side wall and open said cylindrical body.

2. A protective needle cover as claimed in claim 1, wherein said first and said second half side walls are provided at an outer surface with recess portions for a user to conveniently hold said protective needle cover with fingers.

3. A protective needle cover as claimed in claim 1, wherein said projected portion on said second edge of said second half side wall is a hook-like projected member, and wherein said retaining hole on said second edge of said first half side wall is a counterpart of said hook-like projected member so that they together form a set of fastening means to openably close said two half side walls of said cylindrical body of said protective needle cover.

4. A protective needle cover as claimed in claim 3, wherein said hook-like projected member has an inclined front surface and an inclined inner surface, said retaining hole has an inclined sliding surface and an end retaining portion, an engagement of said inclined inner surface of said hook-like projected member with said end retaining portion of said retaining hole permits said set fastening means in a fastened state, and said inclined front surface of said hook-like projected member, when said first and said second half side walls are subject to outcoming opposed forces, slides along said inclined sliding surface of said retaining hole until said inclined inner surface disengages from said end retaining portion.

* * * * *